(12) United States Patent
Kwok et al.

(10) Patent No.: US 9,717,870 B2
(45) Date of Patent: Aug. 1, 2017

(54) METHOD AND APPARATUS FOR MANAGING MOISTURE BUILDUP IN PRESSURISED BREATHING SYSTEMS

(75) Inventors: Philip Rodney Kwok, Bella Vista (AU); Lee James Veliss, Bella Vista (AU); Robert Edward Henry, Bella Vista (AU)

(73) Assignee: ResMed Limited, Bella Vista (AU)

( * ) Notice: Subject to any disclaimer, the term of this patent is extended or adjusted under 35 U.S.C. 154(b) by 3013 days.

(21) Appl. No.: 11/988,541

(22) PCT Filed: Jul. 31, 2006

(86) PCT No.: PCT/AU2006/001081
§ 371 (c)(1),
(2), (4) Date: Jan. 10, 2008

(87) PCT Pub. No.: WO2007/012145
PCT Pub. Date: Feb. 1, 2007

(65) Prior Publication Data
US 2009/0044810 A1 Feb. 19, 2009

Related U.S. Application Data

(60) Provisional application No. 60/703,456, filed on Jul. 29, 2005.

(51) Int. Cl.
*A61M 16/06* (2006.01)
*A61M 16/08* (2006.01)
*A61M 16/10* (2006.01)

(52) U.S. Cl.
CPC ........ *A61M 16/06* (2013.01); *A61M 16/0633* (2014.02); *A61M 16/085* (2014.02);
(Continued)

(58) Field of Classification Search
CPC .............. A61M 16/06; A61M 16/0605; A61M 2205/0205; A61M 2205/0238;
(Continued)

(56) References Cited

U.S. PATENT DOCUMENTS

| 5,595,173 A | 1/1997 | Dodd, Jr. |
| 6,062,220 A | 5/2000 | Whitaker et al. |

(Continued)

FOREIGN PATENT DOCUMENTS

| DE | 197 57 703 | 10/1999 |
| EP | 0 697 225 | 2/1996 |

(Continued)

OTHER PUBLICATIONS

Supplementary European Search Report dated Mar. 1, 2010 (10 pages).

(Continued)

*Primary Examiner* — Justine Yu
*Assistant Examiner* — Michael Tsai
(74) *Attorney, Agent, or Firm* — Nixon & Vanderhye P.C.

(57) ABSTRACT

A washout vent formed of or treated with hydrophobic or hydrophilic material, or a vent coated with hydrophobic or hydrophilic material, reduces noise and/or minimizes or precludes the formation of blockage in the vent pathway due to outflow of gas from a respiratory mask. One or the other or combinations of hydrophobic and hydrophilic materials may be used to repel or wick moisture away to minimize or preclude moisture buildup on vent surfaces and/or clogging of vent pathways, particularly when using humidified air. Sintered porous plastic hydrophobic or hydrophilic materials are utilized and the porosity may be varied integrally within the vent membrane or by forming the vent from layers of materials having different porosities.

39 Claims, 13 Drawing Sheets

(52) U.S. Cl.
CPC . *A61M 16/1045* (2013.01); *A61M 2202/0208* (2013.01); *A61M 2205/42* (2013.01); *A61M 2205/581* (2013.01); *A61M 2205/583* (2013.01); *A61M 2205/7527* (2013.01); *A61M 2205/7536* (2013.01)

(58) Field of Classification Search
CPC ........ A61M 2205/025; A61M 2205/75; A61M 2205/7527; A61M 2205/7536; A61M 2205/7563; A41D 13/11; A41D 13/1107; A41D 2400/60; A41D 2400/62; A62B 18/02; A62B 18/025
USPC ............ 128/206.28, 201.17, 204.18, 205.25, 128/205.27, 206.17, 206.12, 206.21, 128/206.24, 207.13
See application file for complete search history.

(56) References Cited

U.S. PATENT DOCUMENTS

| | | | |
|---|---|---|---|
| 6,258,196 B1 * | 7/2001 | Suzuki et al. | 156/176 |
| 6,561,190 B1 | 5/2003 | Kwok | |
| 6,561,191 B1 | 5/2003 | Kwok | |
| 6,581,594 B1 * | 6/2003 | Drew et al. | 128/204.18 |
| 6,638,610 B1 * | 10/2003 | Yao | 428/304.4 |
| 2004/0255948 A1 * | 12/2004 | Smith et al. | 128/206.15 |
| 2006/0144399 A1 | 7/2006 | Davidowski et al. | |

FOREIGN PATENT DOCUMENTS

| | | | |
|---|---|---|---|
| EP | 1163923 A2 | * | 12/2001 |
| EP | 1 314 445 | | 5/2003 |
| EP | 1314445 A1 | * | 5/2003 |
| GB | 2017529 A | * | 10/1979 |
| JP | 10-028744 | | 2/1998 |
| JP | 2003-135612 | | 5/2003 |
| JP | 2004-261552 | | 9/2004 |
| JP | 2006-122268 | | 5/2006 |
| WO | 95/03114 | | 2/1995 |
| WO | 2005/051468 A1 | | 6/2005 |
| WO | 2006/074516 A1 | | 7/2006 |

OTHER PUBLICATIONS

International Search Report for PCT/AU2006/001081 mailed Oct. 30, 2006.
Written Opinion for PCT/AU2006/001081 mailed Sep. 28, 2006.
U.S. Appl. No. 60/643,114, filed Jan. 12, 2005 (p. 14 of specification).
Extended European Search Report mailed Nov. 28, 2012 in European Application No. 12178212.2 (7 pages).
Communication mailed Aug. 26, 2013 in European Application No. 06 760 938.8 (4 pages).

* cited by examiner

METHOD AND APPARATUS FOR MANAGING MOISTURE BUILDUP IN PRESSURISED BREATHING SYSTEMS

CROSS REFERENCE TO PRIORITY APPLICATION

This application is the U.S. national phase of International Application No. PCT/AU2006/001081 filed 31 Jul. 2006 which designated the U.S. and claims priority to U.S. Provisional Application No. 60/703,456 filed 29 Jul. 2005, the entire contents of each of which are hereby incorporated by reference.

BACKGROUND OF THE INVENTION

The present invention relates to a method and apparatus for managing moisture buildup in humid pressurized breathing systems subject to humidity consideration, etc., e.g., breathable gas supply apparatus for use in Continuous Positive Airway Pressure (CPAP) treatment of Obstructive Sleep Apnea (OSA) and various other respiratory disorders, and diseases. In one example, a respiratory mask is provided with a vent affording reduced noise and/or improved vent flow under humidified gas flow conditions.

CPAP treatment devices typically provide a gas flow generator for delivering pressurized breathable gas, usually air, to a patient's airway using a conduit and mask. In many such devices, the gas flow generator is combined with a humidifier to deliver pressurized humidified gas. The pressurized and optionally humidified gas acts as a pneumatic splint for the patient's airway, preventing airway collapse, especially during the inspiratory phase of respiration. The humidified gas minimizes drying of the nasal mucosa and increases patient comfort. Many standard vents for respiratory masks have adverse reduced flow when used with humidified air, either due to the build up of moisture at the entry to the vent or the blocking of the small gas pathways through the vent. For example, the vent manufactured by Gottlieb Weinmann Gerate Fur Medizin Und Arbeitsschutz GmbH & Co. is known to reduce the vent flow when used with humidified gas. See European Patent No. 0 697 225 A2 to Gottlieb et al. The blockage of the small gas pathways through the vent is a particular problem at low pressures such as 4 cm of $H_2O$ or below. Blockage may occur because pressure is insufficient to keep the pathways clear. In this event, the minimum flow condition for safe $CO_2$ washout may be compromised, especially at the low end of the pressure treatment range.

Further, standard vents, including low noise vents, sometimes encounter obstruction of the gas vent pathway following washing of the mask or vent. Moisture can be retained around the entry or the exit of the vent or within the internal pathways of the vent. At low pressures immediately following a washing of the mask or vent, considerable time may elapse before the moisture is cleared. If the mask is in use while the vent is being cleared, the system has reduced airflow leading to undesirable retention of $CO_2$ within the mask.

BRIEF SUMMARY OF THE INVENTION

One aspect of the invention is directed to providing a super quiet vent for use in medical masks, e.g., for sleep apnea treatment. The vent can be in the form of a diffuser vent that can maintain flow even in wet and/or humid conditions.

In another aspect of the present invention, a vent gas flow path is constructed to provide sufficient venting under humidified gas flow conditions, any obstructions in the vent due to moisture in the outflowing gas or remaining after washing being minimized or eliminated.

In another aspect of the present invention, the vent is constructed to displace or reduce the moisture from the venting pathway. This may be accomplished by preventing moisture from entering the vent pathway or facilitating movement of the moisture away from the vent pathway.

It will be appreciated that in many aspects of the present invention, the vent configuration may be disposed or created within the mask shell or maybe disposed in additional piping extending from the mask, in both cases enabling the outflow of gas, e.g., from the inner cavity within the mask, to atmosphere.

In one example of the present invention, there is provided a respiratory mask comprising a mask body having a patient interface at least in part defining a breathing cavity, and a gas washout vent in communication with the cavity and including a porous portion, the porous portion including a hydrophobic or hydrophilic material. The porous portion may take the form of a porous insert, a porous disk, a plastic portion, a porous sintered plastic, a membrane (with one or more holes), a textile and/or a plastic lined with a textile. The porous portion may be made of plastic material, e.g., polyethylene and/or polypropylene, and it may have a granular structure or a surface structure (e.g., smooth, rough, one or more sides). The porosity may be in the range of about 120-220 μm. Depending on the thickness the porous portion may also serve as a filter. 120-220 μm is the ideal range as a balance between having the lowest noise production, adequate resistance to blockage with humidity, and an appropriate size to be included in a mask system. For ideal noise the porosity should be as fine as possible (<120 μm). For ideal resistance to blockage the porosity should be as coarse as possible (>220 μm). A finer porosity vent however requires a much larger surface area to provide sufficient vent flow and a size limit therefore exists as to how low the porosity can be depending on the amount of space provided for the vent in the mask design. To this end, the greatest surface area available is the entire surface of the mask frame, and in the extreme a mask frame could be made entirely of material that has super fine porosity, implementing the finest porosity whilst still affording sufficient vent flow.

In a further embodiment, a respiratory mask comprises a mask body having a patient interface at least in part defining a breathing cavity; and a gas washout vent in communication with the cavity and including a textile material on one side of the vent for wicking away moisture from the vent.

In a further embodiment, a respiratory mask comprises a patient interface defining an opening communicating between a breathing cavity and an exterior of the patient interface, and a moisture retention channel formed adjacent the opening.

In a further embodiment, a respiratory mask comprises a patient interface defining an opening in communication between a breathing cavity and an exterior of the patient interface, a port in communication with the breathing cavity, wherein the port has at least one portion formed of or treated with a hydrophilic and/or hydrophobic material.

The vent or port may include hydrophobic and/or hydrophilic materials per se, or they may be treated with such. Alternatively, the vent or port or mask generally may simply be made of materials that simulate or have hydrophilic and/or hydrophobic properties.

According to yet another embodiment, there is provided a method for managing moisture and/or humidity in a pressurized breathing system comprising at least a selected portion of the mask manufactured from a material suited to manage moisture and/or humidity.

According to yet another embodiment there is provided a vent assembly including porous material having different porosities in different regions.

These and other aspects will be described in or apparent from the following detailed description of preferred or exemplary embodiments.

In another embodiment a variable vent is provided and includes a closure mounted on at least one hydrophilic expansion member. When humid air condenses in the vent and/or on the expansion member, at least some of the condensation is absorbed by the expansion member causing it to expand. Expansion of the expansion member configures the closure in an open configuration whereby air may pass more easily through the vent. The closure may be made from a porous material or a non-porous material having a hole(s) therethrough.

In a further embodiment, a conical hole venting arrangement is provided. A porous plug is positionable within the conical hole (or may be integrally formed therein), and when so arranged, a flange of the plug is disposed on an outside surface of the frame. The volume of the conical plug is greater than it would otherwise be if a cylindrical plug were provided (i.e. one with a diameter corresponding to the small end of the conical plug) and thus advantageously is able to absorb more moisture.

In one alternative embodiment the porous plug includes a core region having a lower level of porosity and a surrounding infill region (of substantially trapezoidal or triangular cross-section) having a higher level of porosity. This arrangement causes moisture absorbed by the core region to wick outwardly and upwardly to allow air to pass through the vent more freely.

In another embodiment the porous plug includes a number of porous substrates disposed transversly across the hole, wherein the material of adjacent substrates have a decreasing level of porosity towards the flange region of the plug. In one embodiment between two and five porous substrates are provided.

DETAILED DESCRIPTION OF EMBODIMENTS/EXAMPLES

Figure 1:
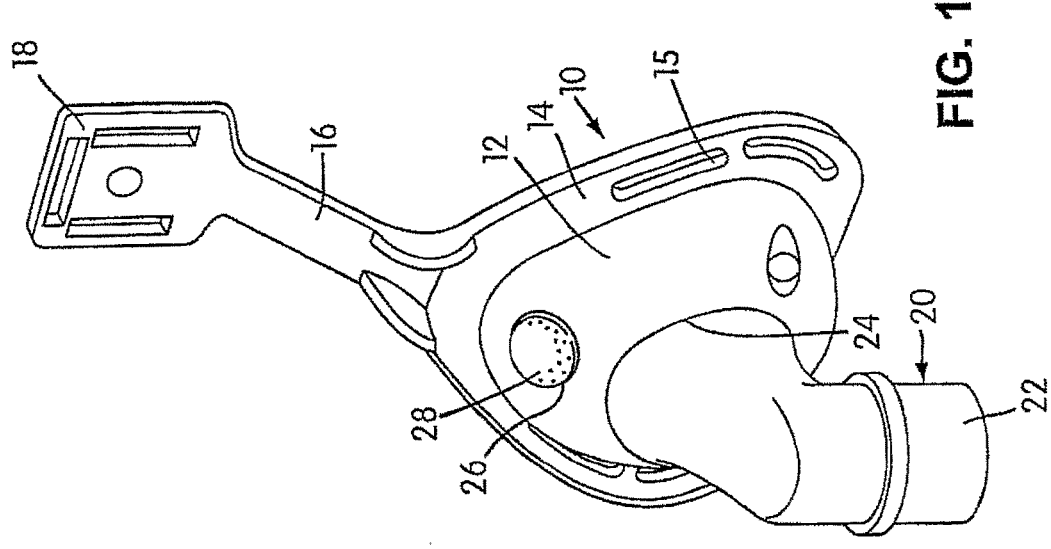
FIG. 1 is a perspective view of a CPAP treatment device in the form of a respiratory mask and illustrating a vent constructed in accordance with a preferred embodiment of the present invention.

FIG. 1 illustrates a breathing system in the form of a patient interface, e.g., a nasal respiratory mask 10, according to a first embodiment of the invention. Mask 10 includes a rigid plastic mask shell 12 that has a peripheral flange 14 for mounting a cushion (not shown) to the shell 12. The cushion abuts the wearer's face in use and is well known in the art. The flange 14 includes slots 15 for the connection of mask restraining straps (not shown) that extend around the head of the wearer to maintain the mask 10 adjacent the wearer's face. The straps are also known in the art. The shell 12 also includes an arm 16 which terminates in a fitting 18 adapted to connect to a forehead support (not shown), which is also known in the art.

The mask shell 12 includes a breathable gas inlet 20, e.g., in the form of a swivel elbow that is rotatably mounted to the shell 12. The inlet 20 has a first end 22 adapted for connection with a breathable gas supply conduit (not shown) coupled to a gas generator for supplying gas under pressure. Inlet 20 has a second end 24, which is adapted to connect to and communicate the supplied pressurized gas to the interior of the shell 12 for subsequent communication with the wearer's airway. Mask 10 also includes a gas washout vent including an opening 26 in the shell 12 across which extends porous portion in the form of a thin air permeable membrane 28, e.g., in the form of a porous disk or insert. Alternatively, the porous portion may take the form of a plastic portion, a porous sintered plastic, a textile and/or a plastic lined with a textile. The porous portion may be made of plastic material, e.g., polyethylene and/or polypropylene), and it may have a granular structure or a surface structure (e.g., smooth, rough, etc., on one or more surfaces or sides), and the porosity may be in the range of 120-220 µm. Depending on the thickness the porous portion may also serve as a filter.

Figure 2:
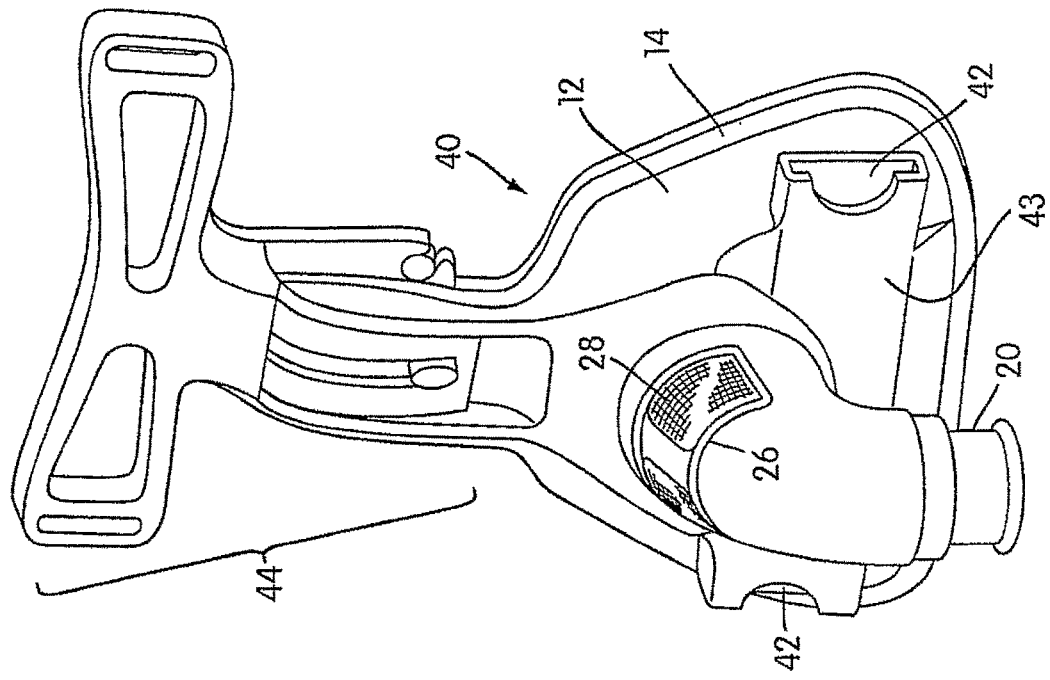
FIG. 2 is a view similar to FIG. 1 illustrating a different preferred configuration of mask and vent.

FIG. 2 discloses a similar nasal respiratory mask 40, wherein like reference numerals are used to describe like parts as in the first embodiment of FIG. 1. Thus, the mask 40 has a shell 12 with a gas inlet 20. Instead of slots 15 of the embodiment of FIG. 1, the mask shell includes openings 42 forming part of a bracket 43, which is adapted to snap engage with connection fittings (not shown) provided on the end of mask restraining straps (also not shown). Instead of the arm 16 and fitting 18, the mask 40 includes an adjustable forehead support mechanism, indicated generally by the reference numeral 44. As in FIG. 1, mask 40 also includes a vent including an opening 26 formed in the gas inlet across which extends a thin permeable membrane 28. While these and other forms of masks are well known, the two forms specifically disclosed herein are representative of the various known forms of masks and the washout vent described below may be utilized in any one or more of those or other known masks.

Figure 3:
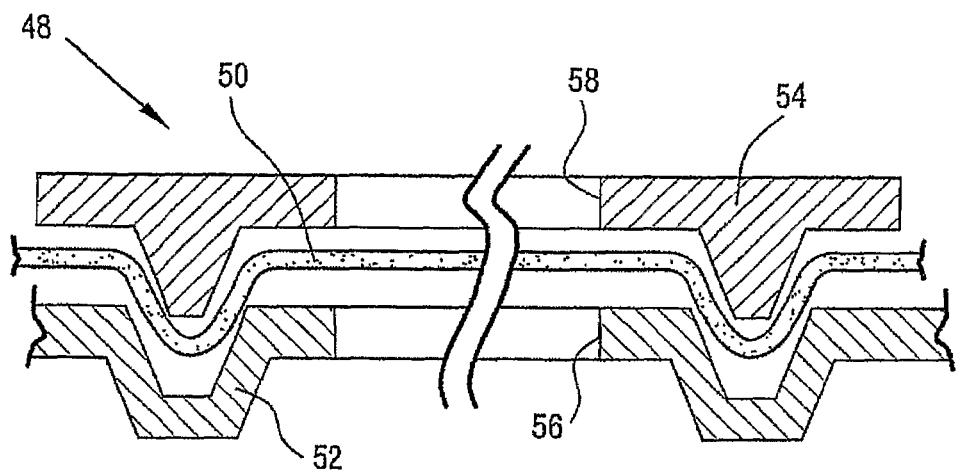
FIGS. 3 and 4 are partial cross-sectional views of a vent assembly according to different embodiments of the present invention.

Referring to FIG. 3, there is illustrated an example of a washout vent 48 according to an aspect of the present invention which includes a membrane 50 interposed between an outer mask element 52 and an inner mask element 54. The membrane 50 is essentially clamped between the two elements. The elements 52 and 54 have registering openings 56 and 58 and the membrane 50 spans across the registering openings 56 and 58. This constitutes only one example of various ways in which the membrane described in detail below may be mounted to the mask.

Figure 4:
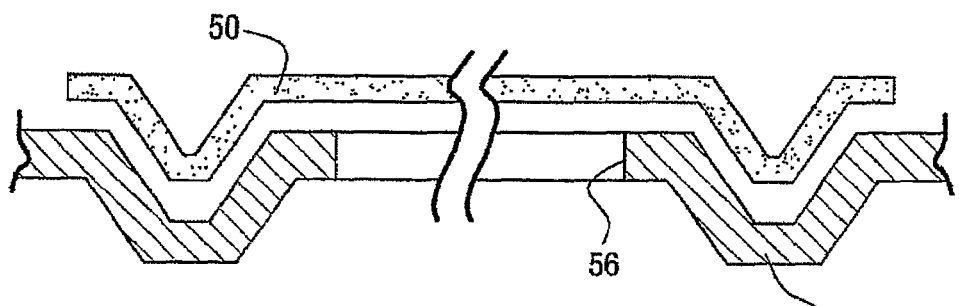

In FIG. 4, there is illustrated another way of mounting the membrane 50, similarly as in FIG. 3, spanning the opening 56 of an outer mask element 52. In this embodiment the membrane 50 is secured solely to the inner surface of the outer element 52 and is not clamped between the two elements.

Figure 5:
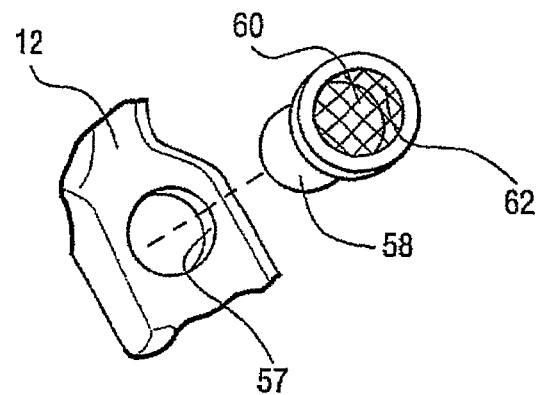
FIG. 5 is a fragmentary perspective view illustrating a mask having a removable vent.

In FIG. 5, the mask shell 12 has an opening 57, which receives a removable holder 58. Holder 58 is preferably hollow and cylindrical and is releasably retained in the opening 57. The holder 58 includes an interior membrane 60 spanning the orifice through holder 58. A grid 62 is carried by holder 58 outwardly of the membrane 60 for protecting the membrane 60. It will be appreciated that the various membranes 25, 58 and 60 disclosed in drawing FIGS. 1-5 are representative only of various configurations and constructions of membranes for the vents for respiratory masks in general and that the membranes as discussed in more detail below have applicability to various other masks having vents for venting gas, particularly humidified gas, from respiratory masks.

Vent—Hydrophobic and/or Hydrophilic Materials

In an aspect of the present invention, the membranes illustrated in FIGS. 1-5 are preferably formed of or coated with a hydrophobic material. Alternatively, the membranes could be treated with surface affecting processes, e.g., nano treatment, coating, etc., similar to concrete treatment. A surface formed of or otherwise having hydrophobic properties of hydrophobic material repels moisture and water droplets. Consequently, if the vent surfaces or the entry to the vent surfaces are formed of hydrophobic material, the surfaces will resist moisture build up through the gas pathways of the vent as well as at the entry to the vent. The surfaces repel the moisture or water droplets and encourage the moisture or water droplets to run off the contacted hydrophobic surfaces. The hydrophobic material may be porous portion in the form of a porous plastic material and formed from such porous plastics as polyethylene, polypropylene, PVDF and PTFE. These materials naturally resist water entry into their pores. These materials are preferably sintered to form the porous construction. Alternatively, the material may be derived from a reticulated or cellular/matrix structure creating one or a plurality of small tortuous paths for gas.

There are many different forms of vent constructions and configurations. In certain vent configurations, the formation of the membrane of, or providing a vent coated with hydrophobic material, will cause a moisture droplet to sit higher off the vent surface. This may increase its proximity to the opposite vent surface tending to block the vent pathway. In those situations, vents formed of or coated with a hydrophilic material are beneficial. The formation of the vent or coating or otherwise treating or providing the vent with a hydrophilic material reduces the tendency of the moisture to remain within and block the vent pathway. As the moisture approaches the exit of the vent, the hydrophilic surfaces wick away the moisture thereby reducing blockage of the vent gas flow. Alternatively or in addition, the hydrophilic surface simply allows the air to pass because the droplet has a low profile.

Figure 5A:
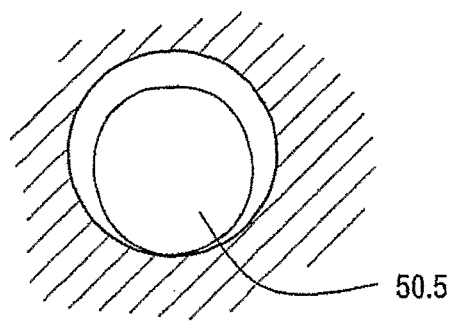
FIGS. 5a-5b illustrate graphically the difference of how hydrophilic and hydrophobic materials interact with water, where the size of the orifice (that a droplet resides in) approaches the size of the droplet.
Figure 5B:
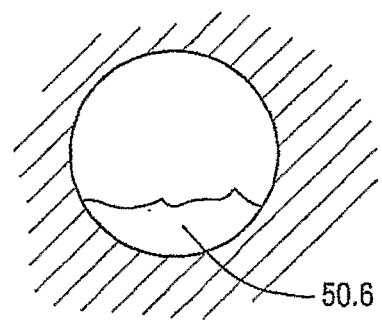

For example, FIG. 5a shows a vent hole 50.5 having a diameter defined by an inner surface that is formed or treated with a hydrophobic material, while FIG. 5b shows a similar vent hole 50.6 provided or treated with a hydrophilic material. Each vent hole 50.5, 50.6 is approximately the same size, yet the water droplet in FIG. 5a tends to more fully occlude the vent hole as compared to the relatively more open vent hole in FIG. 5b.

Figure 5C:
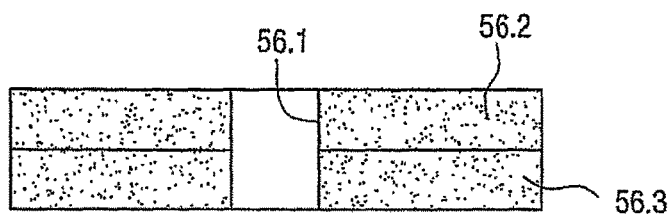
FIGS. 5c-5f are partial cross-sectional views of vent assemblies according to embodiments of the present invention.
Figure 5D:
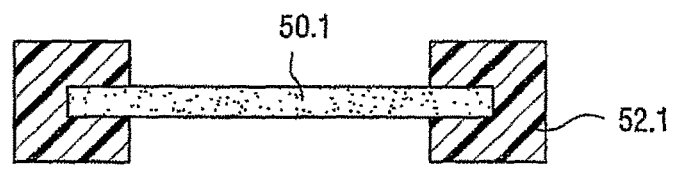
Figure 5E:
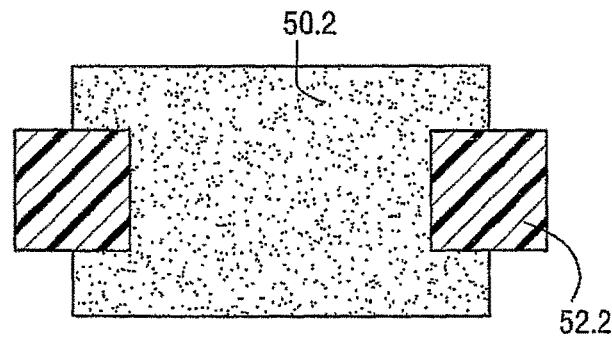
Figure 5F:
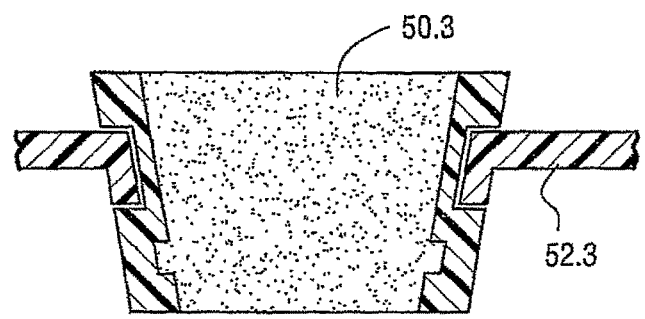

Various combinations of materials may be used to achieve the desired effect. For example, as shown in FIG. 5c, the vent hole 56.1 may have a cross-section having a composite or laminate construction, e.g., including two or more layers, such as a hydrophilic layer 56.2 and a hydrophobic layer 56.3. FIG. 5d shows a relatively thin porous portion having a thickness of around 1-2 mm, in the form of a membrane 50.1 that is thinner than the adjacent wall/frame structure 52.1 supporting the porous portion. FIG. 5e shows a relatively thick porous portion having a thickness of 1 to 20 mm and preferably 3 to 7 mm. The relatively thick porous portion is in the form of a porous disk (e.g., a depth filter 50.2—a filter that has some depth to it (not a thin filtration membrane)) that is thicker than the supporting frame/wall 52.2. FIG. 5f is a cross-section of a porous portion in the form of a snap-fit plastic member 50.3 that is removable/attachable to a frame 52.3.

Another use of hydrophilic material, aside from the collection or channeling of moisture, is to prevent moisture from blocking and/or adversely affecting other parts or ports of the mask used to convey gas. For example, most masks include a pressure port or an $O_2$ therapy port on the frame (e.g., frame 12 in FIG. 1) which can be fitted for formed with a hydrophilic material to prevent fouling of the port. This aspect and other aspects of the invention may be applied to any fluid (e.g., air) transmission orifice or orifices whereby control or management of moisture is desirable.

Porous Plastic Sintered Materials

As with hydrophobic materials, the hydrophilic material may comprise a porous plastic material, such as hydrophilic polyethylene manufactured by Porex Corporation of Fairburn, Ga. Other suitable material such Porex Porous Plastic and Oriented Fiber hydrophilic products can be designed to wick moisture and water droplets at different rates. See, for example, U.S. Pat. No. 6,638,610, issued Oct. 28, 2003, incorporated herein by reference. While "Porous Plastic" may be naturally hydrophobic, such material can be made hydrophilic if treated, e.g., with a surfactant.

When using the Porex hydrophilic products, such as Porex Product XM1839PE (Polyethylene), the pore size may be 120-270 µm, preferably 170-220 µm, and the product may have a 5-35 mm diameter (e.g., about 20 mm) and a 1-10 mm thickness (e.g., about 5 mm). It has been found that these dimensions result in a balance of low noise and maintaining adequate flow even in humid conditions. The use of hydrophilic sintered plastic vents affords efficient airflow for $CO_2$ removal while eliminating much of the vent flow noise associated with traditional venting methods. The vents are produced in plastic moldings preferably using a sintering process and may be molded into any geometry achievable by injection molding technology. The materials used in the mask and vent may be co-moldable and thereby facilitate or eliminate assembly issues. The vent may also be located in any pathway component of the mask, such as the frame, elbow, cushion clip, forehead support, anti-asphyxia valve, cushion or swivel, or air supply or venting pipes. Further, the interface component, e.g., mask frame, can be manufactured from the stated materials, therefore providing a number of utilities or functions for components, thus potentially reducing the number of parts, which can result in ease of use and reduced manufacturing costs. For example, the entire frame 12 of FIG. 1 or the elbow 20 of FIG. 2 could be made of the stated materials. Moreover, the feature or component including the materials can be an add-on, molded-on, retrofit or completely integral. The hydrophilic porous plastic, such as the Porex Porous Plastics noted above, is advantageous in that it can be easily cleaned with a mildly abrasive cleanser to remove dirt, grease, smudges and the like. Heavy grease or oils may be removed with a solvent.

As illustrated in drawings FIGS. 1 and 2, the gas, e.g., air, passes through the sintered plastic hydrophobic or hydrophilic material such that the pressure difference between the inside of the mask or other piping and the atmosphere drives the gas through the fine pores of the material itself into the atmosphere. This has the effect of exhausting the air to atmosphere in a highly diffuse manner. Forcing the gas through the tiny tortuous paths in the sintered plastic material generates a high magnitude of viscous loss in the air. This causes the air to vent to atmosphere at very low velocity for a given bulk flow rate, and hence produces minimal noise. A generally higher surface area is required for vents of this type as compared with conventional venting orifices. The required area will depend greatly upon the porosity and thickness of the material used for the vent. Note that porous materials have been used previously for washout vents. See, for example, U.S. Pat. No. 6,581,594, as well as European Patent No. 0 697 225 A2 to Gottlieb et al. This European patent discloses a vent formed from a porous sintered material. However, the porosity and thickness of the vent for use in the present invention differs considerably from the Gottlieb et al. vent. Gottlieb et al. discloses a generally cylindrical insert, including a window, covered with a porous sintered material of approximately 3-4 mm thickness, but with a much finer porosity than set forth herein. The large pore size of the washout vent membranes herein also provide a flatter pressure flow curve, which is preferable to provide more vent flow at low pressures and less vent flow at high pressures.

Variable Porosity

Figure 6A:
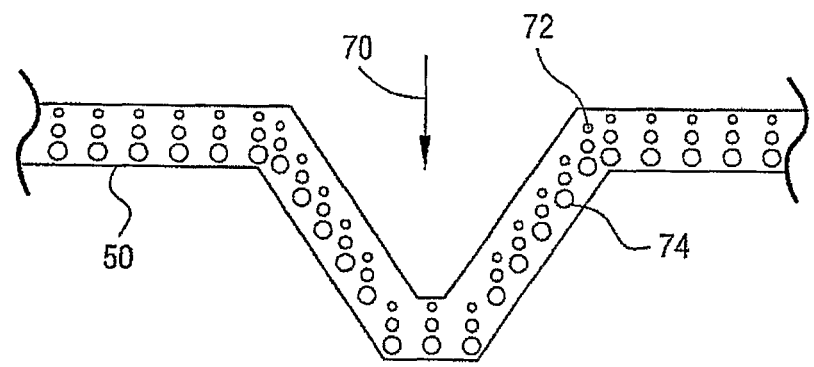
FIGS. 6a-6c illustrate various embodiments of vent material with variable porosity.
Figure 6B:
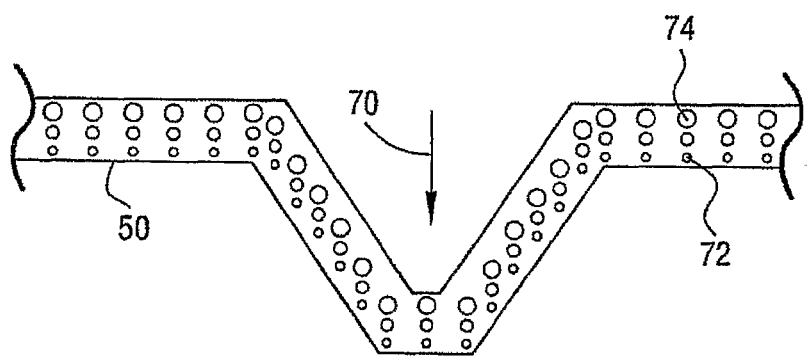
Figure 6C:
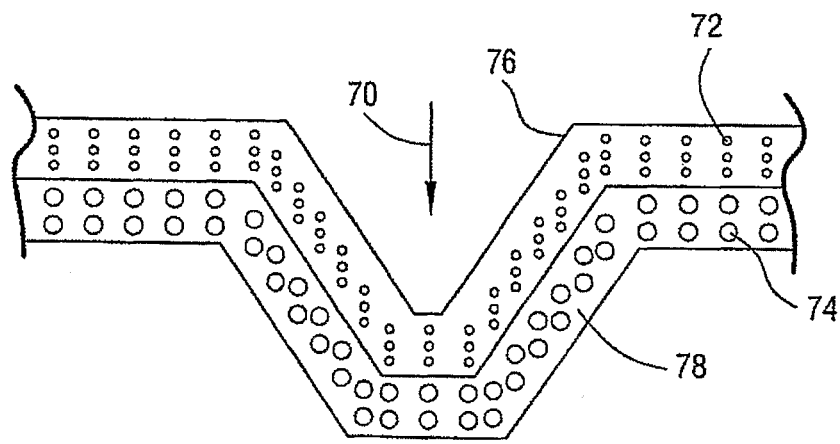

Referring now to FIGS. 6a-6c the vent membranes may be formed of a hydrophobic or hydrophilic material, which has variable porosity across the thickness of the membrane. Variable porosity in these materials may be achieved in the manufacturing process or by using a layer of material having a variable porosity. For example, as illustrated in FIG. 6a, the hydrophobic or hydrophilic sintered porous plastic material forming the membrane 50 may have a fine pore size present at the entry to the vent and a larger pore size at the exit of the vent. The direction of the gas flow venting through the membrane 50 is represented by the arrow 70. In FIG. 6a, the fine pore size is represented by the smaller circles 72 within the membrane adjacent the gas entry surface of the membrane in contrast to the larger pore size represented by the circles 74 adjacent the opposite gas exit surface of the membrane. In FIG. 6b, the reverse configuration is illustrated. That is, the hydrophobic or hydrophilic sintered porous plastic material may have the coarse pore size 74 at the entry surface of the vent and the finer pore size at the exit surface of the vent. A particular advantage of the use of a variable porosity material is that it enables a surface which is less likely to be blocked by moisture to be presented to highly humidified gas at the entry of the vent and a surface that is less likely to be blocked by dirt to reside at the exit of the mask where it may come into contact with dirt or grease.

Referring to FIG. 6c, variable porosity of the membrane may be achieved by layering materials of different porosities. For example, as illustrated in FIG. 6c, the entry to the vent membrane represented by the small circles 72 may be formed of a hydrophobic or hydrophilic sintered plastic material having the fine pore size in a first layer 76 on the entry side of the vent. An exit 78 formed of a hydrophobic or hydrophilic sintered plastic material having a coarse pore size represented by the larger circles 74 may be provided on the opposite side of the vent. Additionally, the interior layer may be formed of hydrophobic material covering or partly covering a hydrophilic layer which is at the exterior of the mask. With this construction, surface moisture tends to run off the vent with the hydrophilic layer encouraging humidified gas to flow through the vent. Alternatively, the hydrophilic material may constitute an interior layer at the entry to the vent, i.e., about the interior of the mask encouraging the humidified gas to flow through the vent. The exterior layer constituted by the hydrophobic material may encourage moisture, e.g., remnants of moisture from a prior washing of the vent, to run off the vent and mask and prevent blocking of the vent.

Moisture Collection Channel

Figure 7A:
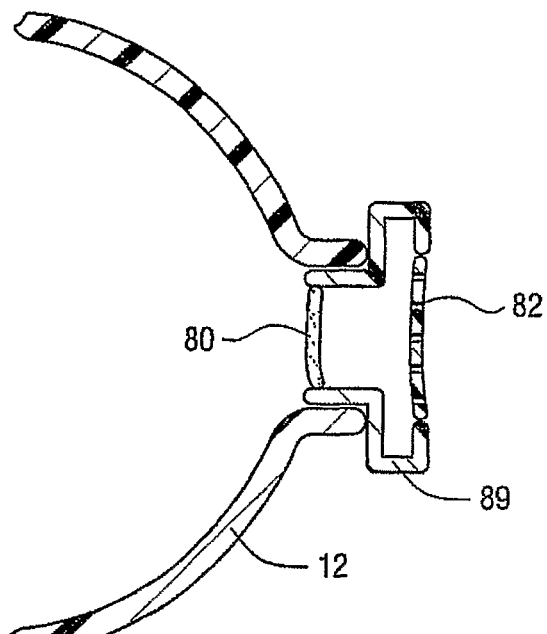
FIG. 7a is a fragmentary cross-sectional view of a vent channel for removing moisture prior to the gas flow encountering the vent.

Referring to FIG. 7a, a layer 80 of either hydrophilic and/or hydrophobic porous material may be positioned prior to the gas entry to the vent 82. This inhibits build up of moisture at the entry of the vent. In the case of hydrophobic material, the interior layer 80 may only be partial, e.g., donut shaped or annular, thus allowing humidified gas to pass unfiltered through an opening in the center of the layer, or other openings thereof, but still preventing the build up of moisture about the entry to the vent. The vent 82 may be formed of conventional vent material, such as sintered metal or may be formed of the hydrophobic or hydrophilic material. The material may also be structured to increase the surface area within a smaller overall size vent. Increased surface area may be implemented using pleats, etc.

Figure 7B:
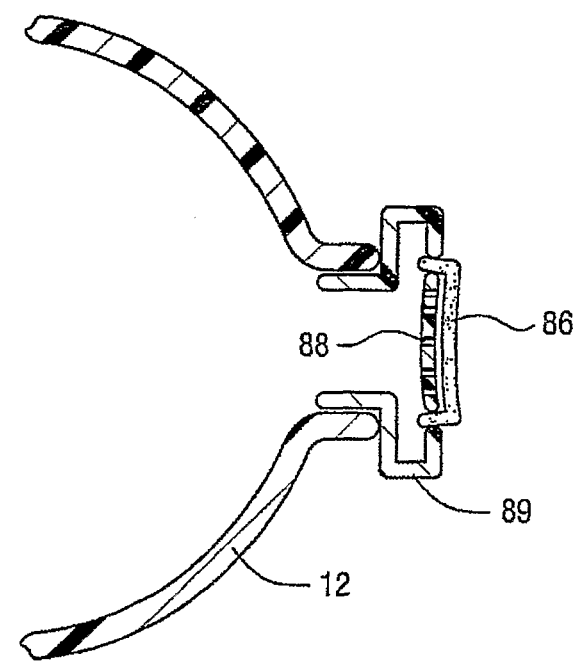
FIG. 7b is a view similar to FIG. 7a illustrating a vent channel adjacent the exit of the vent.

In FIG. 7b, a layer 86 of hydrophilic or hydrophobic porous material is positioned adjacent the exit side of the vent 88. In both cases using the hydrophobic or hydrophilic materials tends to flow moisture away from the vent openings.

The embodiments of FIGS. 7a and 7b include a washout vent structure mounted on a selectively removable holder similar to that shown in FIG. 5. However, the vent could also be mounted directly on the frame (or along another portion of the gas delivery path), e.g., as described in U.S. Pat. Nos. 6,561,190 and 6,561,191, incorporated herein by reference in its entirety).

Further, the embodiments of FIGS. 7a and 7b may include a moisture collection area, e.g., in the form of a trough or channel that may be placed in the vicinity of the opening of the frame. In the example illustrated, the trough is in front of the opening, but it could also be positioned on the inside of the frame.

Roughened Surface

Figure 8A:
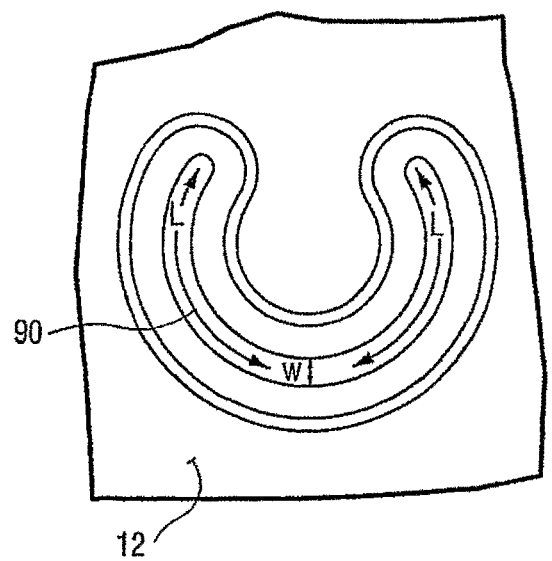
FIG. 8a is an enlarged fragmentary view of a vent in a respiratory mask according to a further embodiment of the present invention.
Figure 8B:
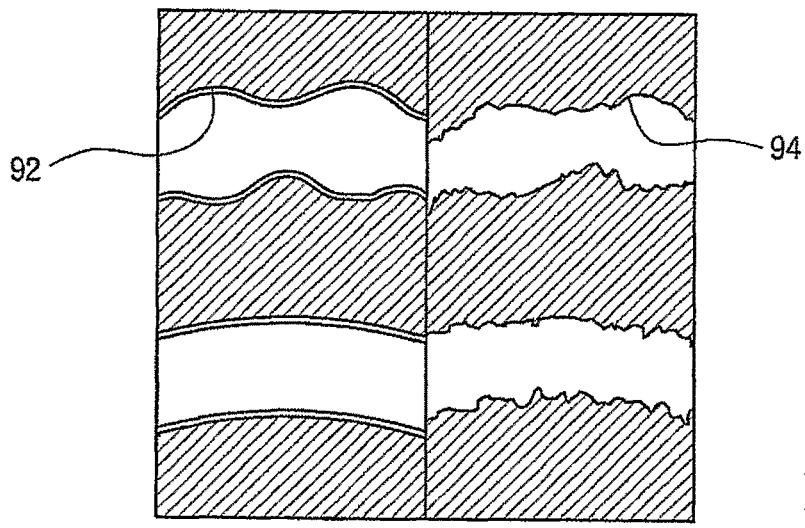
FIG. 8b shows side-by-side cross-sectional comparative views of vent pathways with smooth and roughened surfaces, respectively.
Figure 8C:
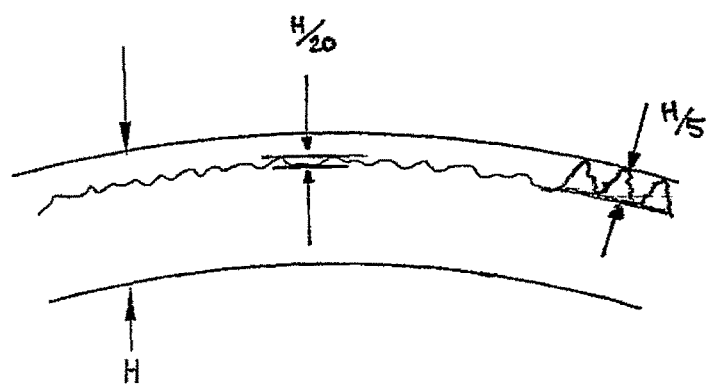
FIG. 8c graphically illustrates roughness measurement of a vent orifice according to an embodiment of the present invention.

Referring to FIG. 8a, there is illustrated a further form of vent disclosed more particularly in U.S. Patent Application Ser. No. 60/643,114, filed Jan. 12, 2005, incorporated herein by reference in its entirety. As described and illustrated in that application one of the preferred vents comprises a generally U-shaped passage 90. Vent 90 and optionally the overall mask frame where the vent is situated may be formed of the porous, sintered plastic hydrophobic and/or hydrophilic materials described herein. The surfaces of the vent passage 90 may have a roughened finish. In FIG. 8b, the left side of the drawing figure illustrates vent passages 92 which are continuous and smooth, albeit the walls of the passages undulate. The masks are made of molded polycarbonate, and may even have a small degree of roughness. In the right side of FIG. 8b, the walls of the passages 94 are illustrated as having highly roughened surfaces (e.g., like the roughened surfaces which are generated using rapid prototype components (Objet®/SLA)—component made from a rapid prototyping process using stereolithography which deposits consecutive fine layers of plastic material according to input from a 3-D CAD model. Roughened surfaces of hydrophobic or hydrophilic material are particularly desirable as the vents produce reduced noise. The roughness can be quantified in terms of the ratio of the thickness of the roughened portion in relation to the overall height (or diameter) (H) of the orifice, as shown in FIG. 8c. The roughness (R) should be in the range of $H/50<R<H/2$, and preferably $H/10<R<H/5$. Thus, if H is 0.7 mm, the roughness R will be between about 0.07 mm and 0.14 mm. In the example of FIG. 8c, an exemplary roughness of H/20 is shown in one region and a preferred roughness of H/5 is shown in another region. The dimension is defined as the height difference between the trough and the apex of the asperity. Thus, by molding vent components out of a plastic material, a roughened surface finish (like that shown on the right side of FIG. 8b) can be utilized as a noise reduction mechanism, while the properties of the hydrophobic or hydrophilic materials assist in moisture management, e.g., to wick moisture and/or to maintain the vent orifices open thereby minimizing risk of blockage with moisture.

Membrane with Holes

Further, use of non-porous hydrophobic or hydrophilic material, specifically plastic, which contains a number of venting holes (e.g., through holes) each having a diameter of up to 0.8 mm may be utilized. This provides a low noise solution, which will not significantly block humidified gas. Alternatively, the vent may be formed from non-hydrophilic or non-hydrophobic material and later coated with hydrophilic or hydrophobic material. The preferred arrangement is similar to that described in the stainless steel embodiment of U.S. Pat. No. 6,581,594, where the holes are smaller than 0.2 mm in diameter. In a further preferred embodiment (similar to the stainless steel embodiment provided in U.S. Pat. No. 6,581,594), the vent has a thickness of approximately 0.45 mm and a number of holes, each hole having a diameter of approximately 0.1 mm. The total open area of such a stainless steel membrane is approximately 5%. However, the vent geometry may take the form of any tapered or non-tapered vent geometry that is known in the art with a hydrophilic or hydrophobic coating enhancing the use of the vent with humidified air.

Wicking Textiles

Figure 9A:
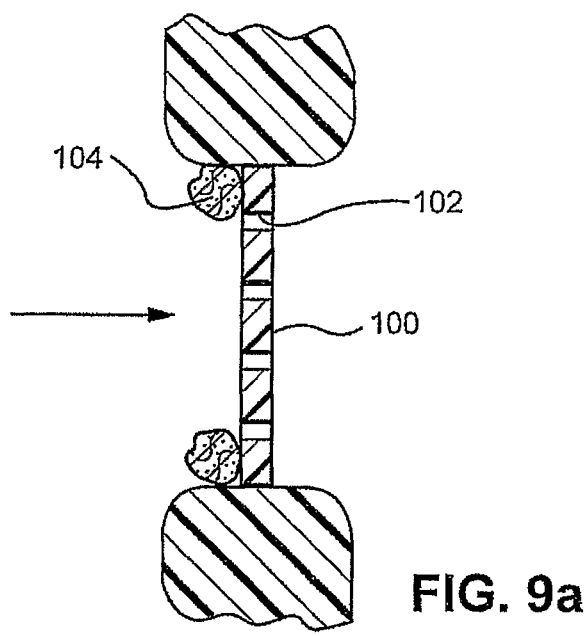
FIGS. 9a-9c are schematic illustrations of further vent arrangements hereof.
Figure 9B:
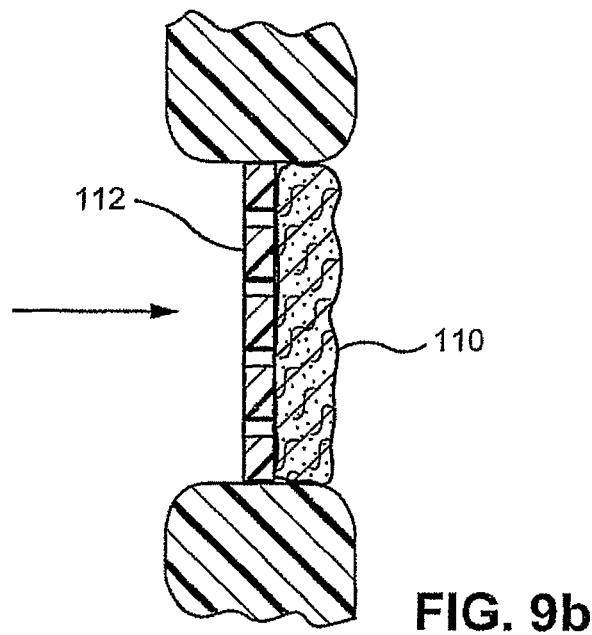
Figure 9C:
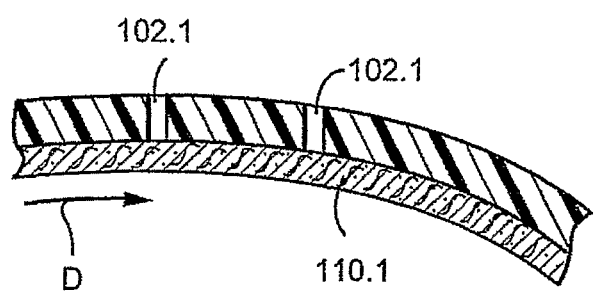

In a further embodiment, a laminated textile may be used to provide the vent so that the vent has self-wicking capability. For example, in FIG. 9a, a plastic vent 100 containing small holes 102 may be provided as a low noise solution vent surrounded by a cotton based material 104 that has a capillary action. Thus, the cotton material 104 surrounding the vent 100 wicks the water from the vent. The wicking action may be along a direction D that is transverse to the axis of the holes 102.1, as shown in FIG. 9c. and can be directed towards an adjacent membrane or part of the same membrane. Alternatively and in FIG. 9b, a textile 110, such as cotton, may be applied as a protective layer in front of the vent 112. The protective layer captures the moisture and acts to wick the moisture away from the vent, while the flow passes through the protective layer and through the small holes in the low noise vent. As well as providing a mechanism for maintaining flow under humidified conditions, an extension of this mechanism is to wick the moisture away to a membrane where it can be subsequently exposed to the breathing gas flow, therefore acting as a humidifier for the breathing gas.

Further, a heated textile or conductive yarn with a current supplied to it (e.g. SoftSwitch as disclosed by Canesis Ltd) can surround the plastic vent or each individual vent hole. The textile prevents condensation of the humidified gas due to the raised temperature of the vent surface. The heated textile may also continue into the air path, e.g., into the mask frame, to increase the exposed area and increase humidity of the breathing gas and/or temperature, especially desirable in cooler climates.

Wicking can be accomplished using a yarn material stitched together closely to allow moisture to capillate between yarns or it may also be at the fiber level, wherein each yarn is capable of capillary action.

The textile fabric that holds moisture can have a dual utility in that the trapped moisture may be rebreathed to assist with moisturizing and/or humidifying the breathing air.

Another way to control the flow through a porous vent under humidification is to draw the moisture away from the vent area using capillary action as will now be described. A mask frame 140 includes a vent assembly 142. The vent assembly 142 has a patient side 144 and an outside 146. The frame 140 includes an orifice 141 having a generally conical shape, with the narrow end of the vent on the patient side 144 of the mask. This will allow more area for the moisture to move to when absorbed. Porous material 148 is arranged within the orifice 141 and extending to the outside of the frame. An additional porous layer 149 would be on the outside of the frame. This extra area would act as a sponge drawing water away from the vent and helping control the vent flow. See FIG. 14.

Using various pore sizes throughout the vent, the path of the moisture can be controlled. Moisture will more readily condensate onto/into materials with a larger surface area.

Figure 14:
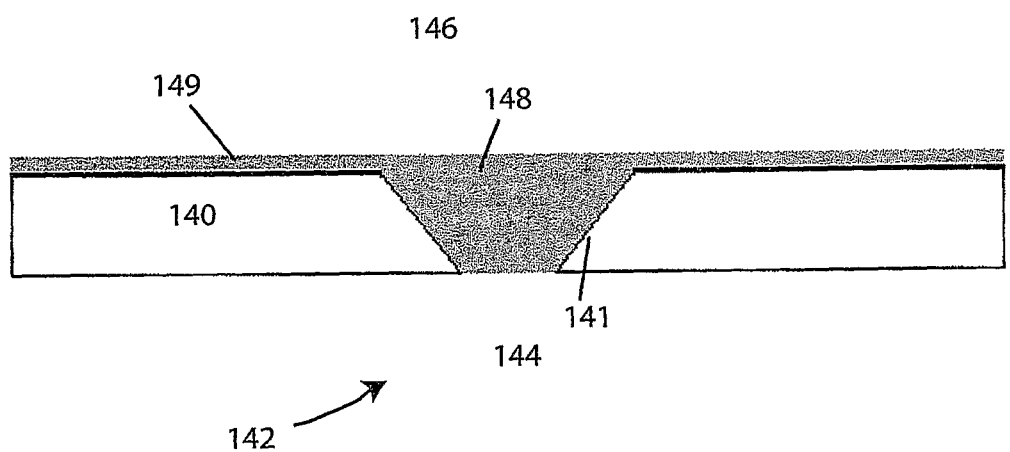
FIG. 14 is a schematic side view of a conical hole venting arrangement according to another embodiment of the present invention, including a porous plug.
Figure 15:
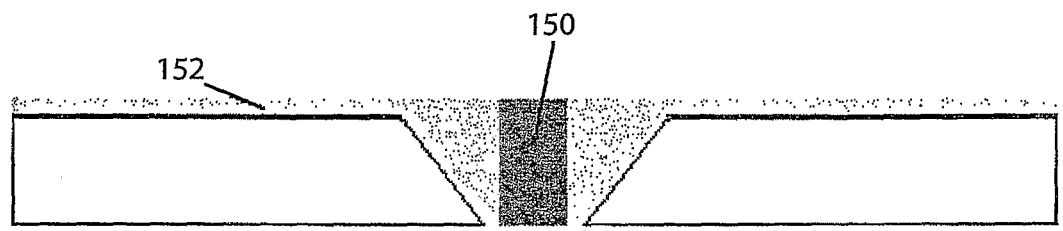
FIG. 15 is a schematic side view of a conical hole venting arrangement according to one embodiment of the present invention, including a plug having a core region of a lower level of porosity and a surrounding infill region having a higher level of porosity.
Figure 16:
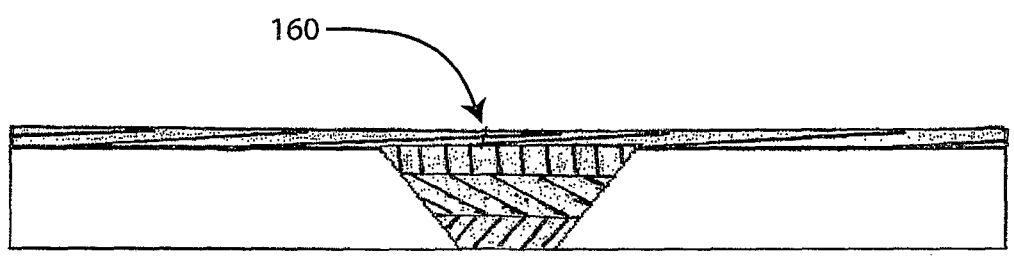
FIG. 16 is a schematic side view of a conical hole venting arrangement according to another embodiment of the present invention, including a plug having a number of porous substrates disposed transversly across the plug, adjacent substrates decreasing in porosity towards an outer substrate.

Another embodiment of the vent of FIG. 14 is shown in FIG. 15. This embodiment involves a core 150 of less porous material surrounded by a more porous outer layer. The more porous area would act as a wick for the moisture to move through. An outer layer on the mask would also be required for moisture dissipation. See FIG. 15 Another embodiment of the above would have multiple layers 160 of porous material that would absorb moisture at different rates. See FIG. 16. Initial condensation will occur on the layer that is on the patient side of the vent. The moisture will then be attracted into the layers above and out to the outer surface of the mask.

Comparative Graphs

Figure 10:
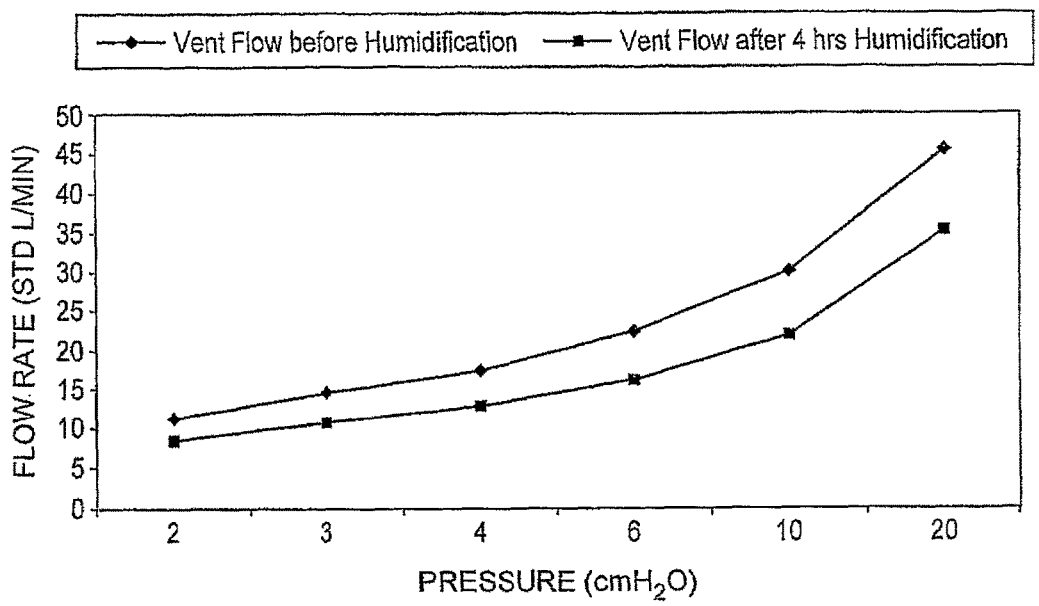
FIGS. 10 and 11 are comparative graphs of flow rate versus pressure, illustrating non-humidified vent flow versus vent flow with humidification.

Referring to FIG. 10, there is illustrated a graph of flow rate through the vent versus pressure using a sintered polyethylene hydrophilic vent before and four hours after humidification. As illustrated in this graph, even with humidified air, the flow rate does not decrease substantially and decreases no more than 15% at any pressure. The flow rate is safe even at low pressures, with and without humidity.

Figure 11:
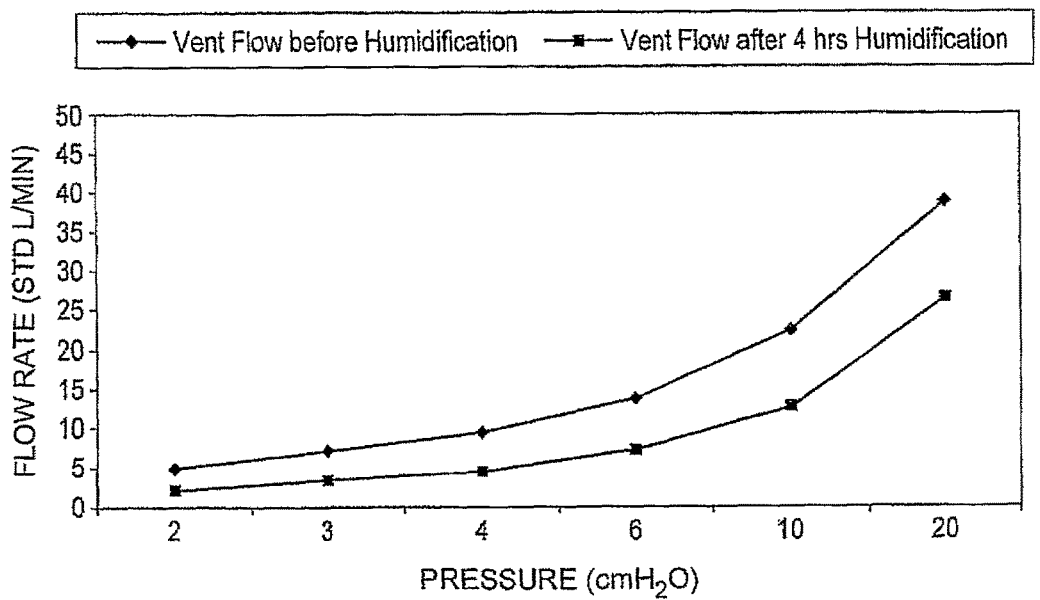

In FIG. 11 there is a similar graph comparing vent flow before humidification and vent flow after four hours of humidification with a sintered porous vent constructed in accordance with the Gottlieb European patent previously identified. This graph illustrates very low flow (potentially unsafe CO2 washout) even without humidity. With humidity, the flow is dangerously low.

Figure 12:
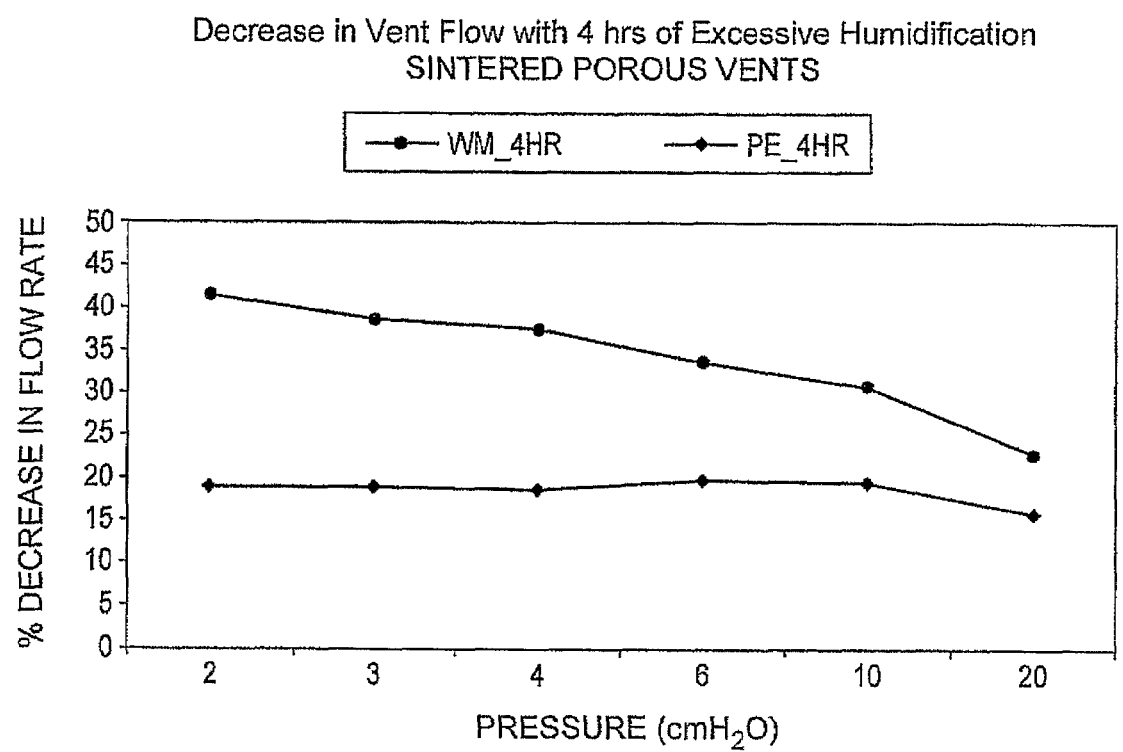
FIG. 12 is a comparative graph of the decrease in vent flow rate versus pressure for a prior art vent and a vent hereof.

In FIG. 12, the graph indicates the percentage decrease in flow rate at various pressures for the Gottlieb sintered porous vent as compared with a sintered polyethylene hydrophilic vent hereof, the performance of which is set forth in FIG. 10. The graph of FIG. 12 demonstrates the decrease in flow rate utilizing the hydrophilic vent structure of an embodiment of the present invention (designated "PE") in comparison with the Gottlieb vent designated "WM". At the desirable low pressures, it will be appreciated that the decrease in flow rate of the present invention is advantageously considerably less than the decrease in flow rate of the Gottlieb vent. The vent designated as "PE" provided adequate flow for $CO_2$ washout, even at lower treatment pressures—both without and with humidity. Gottlieb ("WM") flow falls to below safe levels when humidity is passed through the vent. This vent also takes a considerable amount of time to clear and recover from humidity blockage.

Protective Structure

As illustrated in FIG. 5, an outer protective layer or plate 62 may be provided outside the vent membrane 60 and may comprise a coarse mesh or bars which protects the membrane from damage from large contaminants and handling. Alternatively, the protective plate or mesh may be eliminated if the vent is recessed within the mask frame or within the removable holder 58.

End of Life Indicator

An end-of-life indicator may be mounted on or adjacent to the vent to alert the user to the need to replace the vent. The indicator may provide an indication of the elapsed time that the vent has been in use, blockage of the vent due to humidity or blockage of the vent due to contamination or reduced vent flow rate. The indicator may be either visual or audible. For example, the indicator may include a water soluble dye that gradually washes away, similar to wear indicators provided in some tooth brushes.

Variable Venting

To compensate the hydrophilic nature of the porous vent, a variable vent can be implemented to compensate the flow reduction.

Figure 13A:
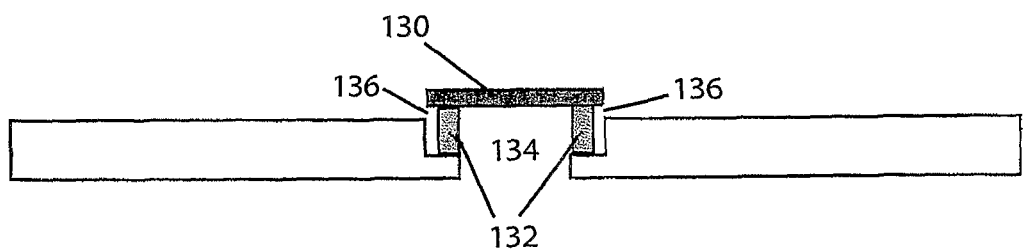
FIGS. 13a and 13b show schematic side views of a variable vent according to a further embodiment of the present invention.

In this form of the invention, a layer of porous material 130 is mounted on feet 132 in a slotted hole 134. The feet 132 are made of a hydrophilic material that expands when moist. This expansion lifts the porous material 130 out of the hole creating a vent in the gap between the frame and vent. See FIG. 13*a*. Crimping the edge of the hole could reduces noise through variable vent.

As the humid air condenses in the vent, it will also be condensing in the feet. In a preferred form the flow reduction in the vent equals the flow increase created by the expanding feet.

Figure 13B:
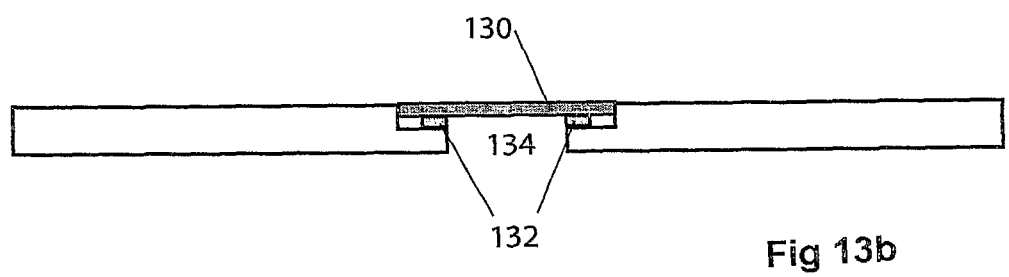

When the feet dry out (release moisture), they will shrink, reducing flow through the variable vent see FIG. 13*b*. In a preferred form the reduction in flow of the variable vent equals the increase in flow through the porous vent as it dries out.

In another form the variable vent is used in conjunction with a traditional vent. Instead of a porous vent being attached to the feet, a nonporous material is used. The flow increase of the variable vent counteracts the flow decrease caused by humidification at the traditional vent.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A respiratory mask comprising:
   a patient interface at least in part defining a breathing cavity; and
   a gas washout vent in communication with said breathing cavity and including a porous portion, said porous portion including at least a surface thereof formed of and/or treated with a hydrophilic material or a hydrophobic material in conjunction with said hydrophilic material.

2. A mask according to claim 1, wherein said porous portion is formed of said hydrophilic material or said hydrophobic material in conjunction with said hydrophilic material.

3. A mask according to claim 1, wherein said porous portion is coated with said hydrophilic material or said hydrophobic material in conjunction with said hydrophilic material.

4. A mask according to claim 1, wherein said porous portion is formed of a sintered hydrophobic material in conjunction with a sintered hydrophilic material or coated with the hydrophobic material in conjunction with the hydrophilic material.

5. A mask according to claim 1, wherein said porous portion is formed of a sintered hydrophilic material or coated with the hydrophilic material.

6. A mask according to claim 1, wherein said porous portion is formed of a sintered hydrophobic material in conjunction with a sintered hydrophilic material.

7. A mask according to claim 1, wherein said porous portion is formed of a sintered hydrophilic material.

8. A mask according to claim 7, wherein said porous portion has a pore diameter in a range of 120-270 µm and a thickness in a range of 1-10 mm.

9. A mask according to claim 8, wherein said sintered hydrophilic material is polyethylene.

10. A mask according to claim 1, wherein said gas washout vent includes a protective element outside of the porous portion.

11. A mask according to claim 1, wherein said porous portion has a pore diameter in a range of 170-220 µm.

12. A mask according to claim 1, including a porous layer of hydrophobic or hydrophilic material upstream of the gas washout vent.

13. A mask according to claim 12, wherein said porous layer of hydrophobic or hydrophilic material includes an opening enabling a portion of expiratory gasses to flow unfiltered to the gas washout vent and another portion of the expiratory gasses to flow through said porous layer of hydrophobic or hydrophilic material for filtering prior to flow to the gas washout vent.

14. A mask according to claim 1, including a porous layer of hydrophobic or hydrophilic material downstream of the gas washout vent.

15. A mask according to claim 1, wherein the gas washout vent includes vent holes having roughened wall surfaces formed of one of said hydrophobic or hydrophilic materials.

16. A mask according to claim 1, wherein the porous portion comprises a membrane that includes a number of holes each having a diameter of up to about 0.8 mm.

17. A mask according to claim 16, wherein the surface of the membrane is formed of a hydrophobic or hydrophilic plastic material.

18. A mask according to claim 1, wherein the porous portion comprises an insert, a disk, a membrane and/or a textile.

19. A mask according to claim 1, wherein the porous portion may have a granular or roughened surface.

20. A mask according to claim 19, wherein the roughness (R) of the surface is in the range of about H/50<R<H/2, where H is the height or diameter of the gas washout vent.

21. A mask according to claim 1, wherein the porous portion is formed in one piece with the patient interface.

22. A mask according to claim 1, wherein the porous portion is treated.

23. A mask according to claim 1, wherein the porous portion includes at least one hole.

24. A mask according to claim 1, further comprising an end-of-life indicator.

25. A respiratory mask according to claim 1, wherein the gas washout vent is produced in a plastic mold using a sintering process.

26. A respiratory mask comprising:
a patient interface at least in part defining a breathing cavity; and
a gas washout vent in communication with said breathing cavity and including a porous portion, said porous portion including at least a surface thereof formed of and/or treated with a hydrophobic or hydrophilic material, wherein a porosity of the porous portion varies between opposite sides thereof, with a pore diameter on one side of the porous portion being greater than a pore diameter on an opposite side of the porous portion.

27. A mask according to claim 26, wherein said porous portion is formed of at least two portions of different material, one of said portions including a hydrophobic material and another of said portions including a hydrophilic material.

28. A mask according to claim 27, wherein the portion including hydrophobic material lies along an interior of the vent and the portion including hydrophilic material lies along an exterior of the vent.

29. A mask according to claim 27, wherein the portion including hydrophilic material lies along an interior of the gas washout vent and the hydrophobic material lies along an exterior of the vent.

30. A mask according to claim 26, wherein the pore diameter on an interior side of the porous portion is greater than the pore diameter on an exterior side of the porous portion.

31. A mask according to claim 30, wherein the pore diameter gradually decreases from the interior side of the porous portion toward the exterior side of the porous portion.

32. A method for managing moisture and/or humidity in a pressurized breathing system comprising:
providing the respiratory mask of claim 1; and
manufacturing at least the gas washout vent of the respiratory mask from a hydrophilic material suited to manage moisture and/or humidity.

33. A method according to claim 32, wherein the gas washout vent comprises a port.

34. A method according to claim 32, wherein the gas washout vent comprises or leads to a collection trough.

35. A method according to claim 32, wherein the gas washout vent is also manufactured from a hydrophobic material.

36. A method according to claim 32, wherein the hydrophilic material comprises a textile material.

37. A mask according to claim 1 wherein the porous portion has different porosities in different regions.

38. A mask according to claim 37 having a core of less porous material surrounded by a more porous outer layer.

39. A mask according to claim 37 including multiple layers of porous material that absorb moisture at different rates.

* * * * *